(12) United States Patent
Boucher et al.

(10) Patent No.: US 11,207,124 B2
(45) Date of Patent: Dec. 28, 2021

(54) ELECTROSURGICAL SYSTEM FOR USE WITH NON-STICK COATED ELECTRODES

(71) Applicant: COVIDIEN LP, Mansfield, MA (US)

(72) Inventors: Todd W. Boucher, Longmont, CO (US); William E. Robinson, Boulder, CO (US); Monte S. Fry, Longmont, CO (US); James D. Allen, IV, Broomfield, CO (US); Jennifer R. McHenry, Denver, CO (US)

(73) Assignee: Covidien LP, Mansfield, MA (US)

( * ) Notice: Subject to any disclaimer, the term of this patent is extended or adjusted under 35 U.S.C. 154(b) by 356 days.

(21) Appl. No.: 16/504,481

(22) Filed: Jul. 8, 2019

(65) Prior Publication Data

US 2021/0007789 A1    Jan. 14, 2021

(51) Int. Cl.
  *A61B 18/12* (2006.01)
  *A61B 18/14* (2006.01)
  *A61B 18/00* (2006.01)

(52) U.S. Cl.
  CPC ...... *A61B 18/1206* (2013.01); *A61B 18/1442* (2013.01); *A61B 18/1445* (2013.01);
  (Continued)

(58) Field of Classification Search
  CPC ............ A61B 18/1206; A61B 18/1442; A61B 18/1445; A61B 2018/0013; A61B 2018/00136; A61B 2018/00666; A61B 2018/00827; A61B 2018/00875; A61B 2018/00892
  See application file for complete search history.

(56) References Cited

U.S. PATENT DOCUMENTS

| 3,729,007 A | 4/1973 | Mirkovitch |
| 4,100,113 A | 7/1978 | McCain |

(Continued)

FOREIGN PATENT DOCUMENTS

| CN | 1649887 A | 8/2005 |
| EP | 0331774 A1 | 9/1989 |

(Continued)

OTHER PUBLICATIONS

Extended European Search Report corresponding to European Application No. 09755793.8, dated Jul. 21, 2014; 8 pages.

(Continued)

*Primary Examiner* — Daniel W Fowler
(74) *Attorney, Agent, or Firm* — Carter, DeLuca & Farrell LLP

(57) ABSTRACT

An electrosurgical system includes an electrosurgical instrument having an electrode with a polymeric dielectric coating; and an electrosurgical generator, which includes a power converter configured to generate RF energy; a sensor coupled to the power converter and configured to sense a parameter of the RF energy; and a controller coupled to the sensor and the power converter. The controller is configured to control the power converter to output an RF waveform to achieve conductor breakthrough through the polymeric dielectric coating. The controller is further configured to determine whether the conductor breakthrough occurred based on the parameter; and execute a treatment algorithm based on a determination of the conductor breakthrough.

20 Claims, 11 Drawing Sheets

(52) U.S. Cl.
CPC ............... *A61B 2018/00083* (2013.01); *A61B 2018/00648* (2013.01); *A61B 2018/00678* (2013.01); *A61B 2018/00702* (2013.01); *A61B 2018/00779* (2013.01); *A61B 2018/00827* (2013.01); *A61B 2018/00875* (2013.01); *A61B 2018/00892* (2013.01)

(56) References Cited

U.S. PATENT DOCUMENTS

| | | |
|---|---|---|
| 4,348,426 A | 9/1982 | Blenner et al. |
| 4,396,450 A | 8/1983 | Blenner et al. |
| 4,492,231 A | 1/1985 | Auth |
| 4,714,650 A | 12/1987 | Obayashi et al. |
| 5,201,900 A | 4/1993 | Nardella |
| 5,211,993 A | 5/1993 | Kolesinski |
| 5,213,928 A | 5/1993 | Yu |
| 5,484,436 A | 1/1996 | Eggers et al. |
| 5,549,604 A | 8/1996 | Sutcu et al. |
| 5,702,387 A | 12/1997 | Arts et al. |
| 5,713,895 A | 2/1998 | Lontine et al. |
| 5,773,098 A | 6/1998 | Thomas |
| 5,925,043 A | 7/1999 | Kumar et al. |
| 5,965,629 A | 10/1999 | Jung et al. |
| 6,066,137 A | 5/2000 | Greep |
| 6,070,444 A | 6/2000 | Lontine et al. |
| 6,139,547 A | 10/2000 | Lontine et al. |
| 6,146,462 A | 11/2000 | Malizis et al. |
| 6,159,531 A | 12/2000 | Dang et al. |
| 6,293,946 B1 | 9/2001 | Thorne |
| 6,300,641 B1 | 10/2001 | Koh et al. |
| 6,408,755 B1 | 6/2002 | Meisters et al. |
| 6,428,861 B2 | 8/2002 | France et al. |
| 6,486,135 B1 | 11/2002 | Li et al. |
| 6,534,133 B1 | 3/2003 | Kaloyeros et al. |
| 6,548,121 B1 | 4/2003 | Bauer et al. |
| 6,582,429 B2 | 6/2003 | Krishnan et al. |
| 6,602,552 B1 | 8/2003 | Daraskevich et al. |
| 6,730,275 B2 | 5/2004 | Sharma et al. |
| 6,774,018 B2 | 8/2004 | Mikhael et al. |
| 6,869,676 B2 | 3/2005 | Burger et al. |
| 6,932,816 B2 | 8/2005 | Phan |
| 6,951,559 B1 | 10/2005 | Greep |
| 6,953,461 B2 | 10/2005 | McClurken et al. |
| 7,067,405 B2 | 6/2006 | Mikhael et al. |
| 7,083,618 B2 | 8/2006 | Couture et al. |
| 7,147,634 B2 | 12/2006 | Nesbitt |
| 7,156,842 B2 | 1/2007 | Sartor et al. |
| 7,214,413 B2 | 5/2007 | Koulik et al. |
| 7,258,899 B1 | 8/2007 | Sharma et al. |
| 7,288,091 B2 | 10/2007 | Nesbitt |
| 7,300,859 B2 | 11/2007 | Mikhael et al. |
| 7,377,919 B2 | 5/2008 | Heim et al. |
| 7,390,326 B2 | 6/2008 | Nesbitt |
| 7,566,333 B2 | 7/2009 | Van Wyk et al. |
| 7,588,565 B2 | 9/2009 | Marchitto et al. |
| 7,618,684 B2 | 11/2009 | Nesbitt |
| 7,683,293 B2 | 3/2010 | Buzzi et al. |
| 7,753,908 B2 | 7/2010 | Swanson |
| 7,899,552 B2 | 3/2011 | Atanasoska et al. |
| 7,955,637 B2 | 6/2011 | Nesbitt |
| 7,967,839 B2 | 6/2011 | Flock et al. |
| 7,976,544 B2 | 7/2011 | McClurken et al. |
| 8,007,494 B1 * | 8/2011 | Taylor ................ A61B 18/1233 606/34 |
| 8,814,861 B2 | 8/2014 | Nesbitt |
| 8,865,264 B2 | 10/2014 | Haack et al. |
| 2001/0045351 A1 | 11/2001 | Koh et al. |
| 2003/0036753 A1 | 2/2003 | Morgan et al. |
| 2003/0158548 A1 | 8/2003 | Phan et al. |
| 2003/0158549 A1 | 8/2003 | Swanson |
| 2003/0229344 A1 | 12/2003 | Dycus et al. |
| 2003/0236518 A1 | 12/2003 | Marchitto et al. |
| 2004/0134770 A1 | 7/2004 | Petersen |
| 2004/0206365 A1 | 10/2004 | Knowlton |
| 2004/0210282 A1 | 10/2004 | Flock et al. |
| 2005/0113828 A1 | 5/2005 | Shields et al. |
| 2005/0203507 A1 | 9/2005 | Truckai et al. |
| 2006/0116675 A1 | 6/2006 | McClurken et al. |
| 2007/0029500 A1 | 2/2007 | Coulombe et al. |
| 2007/0184208 A1 | 8/2007 | Sharma et al. |
| 2008/0050291 A1 | 2/2008 | Nagasawa |
| 2008/0063895 A1 | 3/2008 | Jun et al. |
| 2008/0167398 A1 | 7/2008 | Patil et al. |
| 2009/0102886 A1 | 4/2009 | Sieber et al. |
| 2010/0069904 A1 | 3/2010 | Cunningham |
| 2011/0054461 A1 * | 3/2011 | Dickhans ............. A61B 18/148 606/33 |
| 2011/0137229 A1 * | 6/2011 | Palti ....................... A61N 1/40 604/20 |
| 2011/0270251 A1 | 11/2011 | Horner et al. |
| 2012/0252709 A1 | 10/2012 | Felts et al. |
| 2013/0041355 A1 * | 2/2013 | Heeren ................. A61B 18/14 606/5 |
| 2013/0116682 A1 | 5/2013 | Koo et al. |
| 2017/0119457 A1 | 5/2017 | Sartor et al. |
| 2019/0090934 A1 | 3/2019 | Robinson et al. |
| 2019/0099210 A1 * | 4/2019 | Eggers ................. A61B 18/10 |

FOREIGN PATENT DOCUMENTS

| | | |
|---|---|---|
| EP | 0991365 A4 | 4/2000 |
| EP | 3165189 A1 | 5/2017 |
| EP | 3202350 A1 | 8/2017 |
| JP | 62130777 | 6/1987 |
| JP | 03149797 | 6/1991 |
| JP | 8243755 | 9/1996 |
| JP | 2000286094 A | 10/2000 |
| JP | 2001332399 A | 11/2001 |
| JP | 2003093869 A | 4/2003 |
| JP | 2005522824 A | 7/2005 |
| JP | 2005276618 A | 10/2005 |
| JP | 2006114450 A | 4/2006 |
| JP | 2006310101 A | 11/2006 |
| JP | 2007188748 A | 7/2007 |
| JP | 2007207540 A | 8/2007 |
| JP | 2008041495 A | 2/2008 |
| JP | 2008071656 A | 3/2008 |
| WO | 9513313 A1 | 5/1995 |
| WO | 0016706 A1 | 3/2000 |
| WO | 0145862 A1 | 6/2001 |
| WO | 03/085693 A1 | 10/2003 |
| WO | 03/096880 A2 | 11/2003 |
| WO | 2004094306 A1 | 11/2004 |
| WO | 2009146432 A1 | 12/2009 |
| WO | 2010008062 A1 | 1/2010 |

OTHER PUBLICATIONS

Japanese Notice of Final Rejection and Denial of Entry of Amendment (with English translation), issued Apr. 2, 2015, corresponding to Japanese Patent Application No. 2012-513022; 10 total pages.

Extended European Search Report issued in Appl. No. 10849146.5 dated Sep. 26, 2013; 6 pages.

Japanese Notice of Final Rejection and Denial of Entry of Amendment (with English translation), dated Jun. 2, 2015, corresponding to Japanese Patent Application No. 2013-502548; 15 total pages.

English translation of Japanese Notice of Reasons for Rejection, dated Feb. 18, 2014, corresponding to Japanese Patent Application No. 2013-502548; 6 pages.

English translation of Japanese Notice of Reasons for Rejection, dated Oct. 7, 2014, corresponding to Japanese Patent Application No. 2013-502548; 6 pages.

Australian Patent Examination Report No. 1, dated Apr. 17, 2014, corresponding to Australian Patent Application No. 2010349784; 3 pages.

European Communication dated Jun. 17, 2014, corresponding to European Patent Application No. 10849146.5; 6 pages.

European Communication/Examination Report dated Jul. 14, 2015, corresponding to European Patent Application No. 09 845 329.3; 8 pages.

(56) References Cited

OTHER PUBLICATIONS

European Search Report from Application No. EP 11 00 7711 completed Nov. 4, 2011.
European Search Report from Application No. EP 12191973.2 dated Mar. 20, 2013.
Extended European Search Report from Appl. No. EP 16196104 dated Apr. 7, 2017.
Chinese Office Action issued in Application No. CN 201610972039.9 dated Jul. 31, 2018, together with English language translation (15 pages).
Australian Examination Report dated Dec. 21, 2018 issued in corresponding AU Appln. No. 2018222882.
Extended European Search Report dated Jan. 30, 2019 issued in corresponding EP Appln. No. 18195879 4.
Canadian Office Action dated Aug. 29, 2019 issued in corresponding CA Appln. No. 3,015,418.
Extended European Search Report dated Dec. 4, 2020 issued in corresponding EP Appln No. 20184568.2.

\* cited by examiner

ELECTROSURGICAL SYSTEM FOR USE WITH NON-STICK COATED ELECTRODES

BACKGROUND

1. Technical Field

The present disclosure relates to an electrosurgical generator for use with electrosurgical tissue sealing instruments having a non-stick coating disposed on one or more electrodes. More particularly, the present disclosure relates to a system and method of applying electrosurgical energy to overcome the insulative properties on the non-stick coating.

2. Background of the Related Art

Electrosurgical forceps utilize mechanical clamping action along with electrical energy to effect hemostasis on the clamped tissue. The forceps (open, laparoscopic or endoscopic) include sealing plates which apply energy to the clamped tissue. By controlling the intensity, frequency and duration of the energy applied through the sealing plates to the tissue, the surgeon can cut, coagulate, cauterize, and/or seal tissue.

In the past, efforts have been made to reduce the sticking of soft tissue to the sealing plate during application of energy. In general, such efforts have envisioned non-stick surface coatings, such as polytetrafluoroethylene (PTFE, commonly sold under the trademark TEFLON®) for increasing the lubricity of the tool surface. However, these materials may interfere with the efficacy and efficiency of hemostasis. Accordingly, there is a need for electrosurgical generators configured to operate with electrosurgical instruments having a non-stick coating disposed on one or more electrodes.

SUMMARY

Electrosurgical instruments described herein include at least one tissue sealing plate including a non-stick coating configured to reduce the sticking of soft tissue to the sealing plate during application of energy.

According to one embodiment of the present disclosure, an electrosurgical system is provided. The electrosurgical system includes an electrosurgical instrument having an electrode with a polymeric dielectric coating; and an electrosurgical generator, which includes a power converter configured to generate RF energy; a sensor coupled to the power converter and configured to sense a parameter of the RF energy; and a controller coupled to the sensor and the power converter. The controller is configured to control the power converter to output an RF waveform to achieve conductor breakthrough through the polymeric dielectric coating. The controller is further configured to determine whether the conductor breakthrough occurred based on the parameter; and execute a treatment algorithm based on a determination of the conductor breakthrough.

According to one aspect of the above embodiment, the controller is further configured to compare the parameter to a set threshold indicative of the conductor breakthrough. The controller is further configured to control the power converter to output the RF waveform for a set period of time and to execute the treatment algorithm based on the determination of the conductor breakthrough occurring within the set period of time.

According to another aspect of the above embodiment, the parameter that is measured is impedance and the controller is further configured to compare the measured impedance to a set impedance threshold. The controller is further configured to execute the treatment algorithm in response to the measured impedance being below the set impedance threshold and to adjust a power setting of the treatment algorithm prior to the execution of the treatment algorithm in response to the measured impedance being above the set impedance threshold. The controller is further configured to adjust a power setting of the RF waveform in response to the measured impedance being above the set impedance threshold.

According to a further aspect of the above embodiment, the parameter that is measured is one of voltage or current and the controller is further configured to compare the measured voltage and/or current to a set voltage and/or current threshold.

According to another embodiment of the present disclosure, a method is provided. The method includes electrically coupling an electrosurgical instrument to an electrosurgical generator. The electrosurgical instrument includes an electrode having a polymeric dielectric coating. The method further includes controlling a power converter of the electrosurgical generator to output an RF waveform to achieve conductor breakthrough through the polymeric dielectric coating and sensing at least one parameter of the RF waveform at a sensor of the electrosurgical generator. The method further includes determining at a controller of the electrosurgical generator whether the conductor breakthrough occurred based on the at least one parameter and executing a treatment algorithm at the controller based on a determination of the conductor breakthrough.

According to one aspect of the above embodiment, determining whether the conductor breakthrough occurred further includes comparing the at least one parameter to a set threshold indicative of the conductor breakthrough. The method further includes outputting the RF waveform for a set period of time. Further, the treatment algorithm is executed based on the determination of the conductor breakthrough occurring within the set period of time.

According to another aspect of the above embodiment, the method further includes measuring impedance; and comparing the measured impedance to a set impedance threshold. The method further includes executing the treatment algorithm in response to the measured impedance being below the set impedance threshold. The method further includes adjusting a power setting of the treatment algorithm prior to the execution of the treatment algorithm in response to the measured impedance being above the set impedance threshold. The method further includes adjusting a power setting of the RF waveform in response to the measured impedance being above the set impedance threshold.

According to another aspect of the above embodiment, the method further includes measuring voltage and/or current and comparing the measured voltage and/or current to a set voltage and/or current threshold.

BRIEF DESCRIPTION OF THE DRAWINGS

The above and other aspects, features, and advantages of the present electrosurgical tissue sealing instruments will become more apparent in light of the following detailed description when taken in conjunction with the accompanying drawings in which.

DETAILED DESCRIPTION

Figure 1:
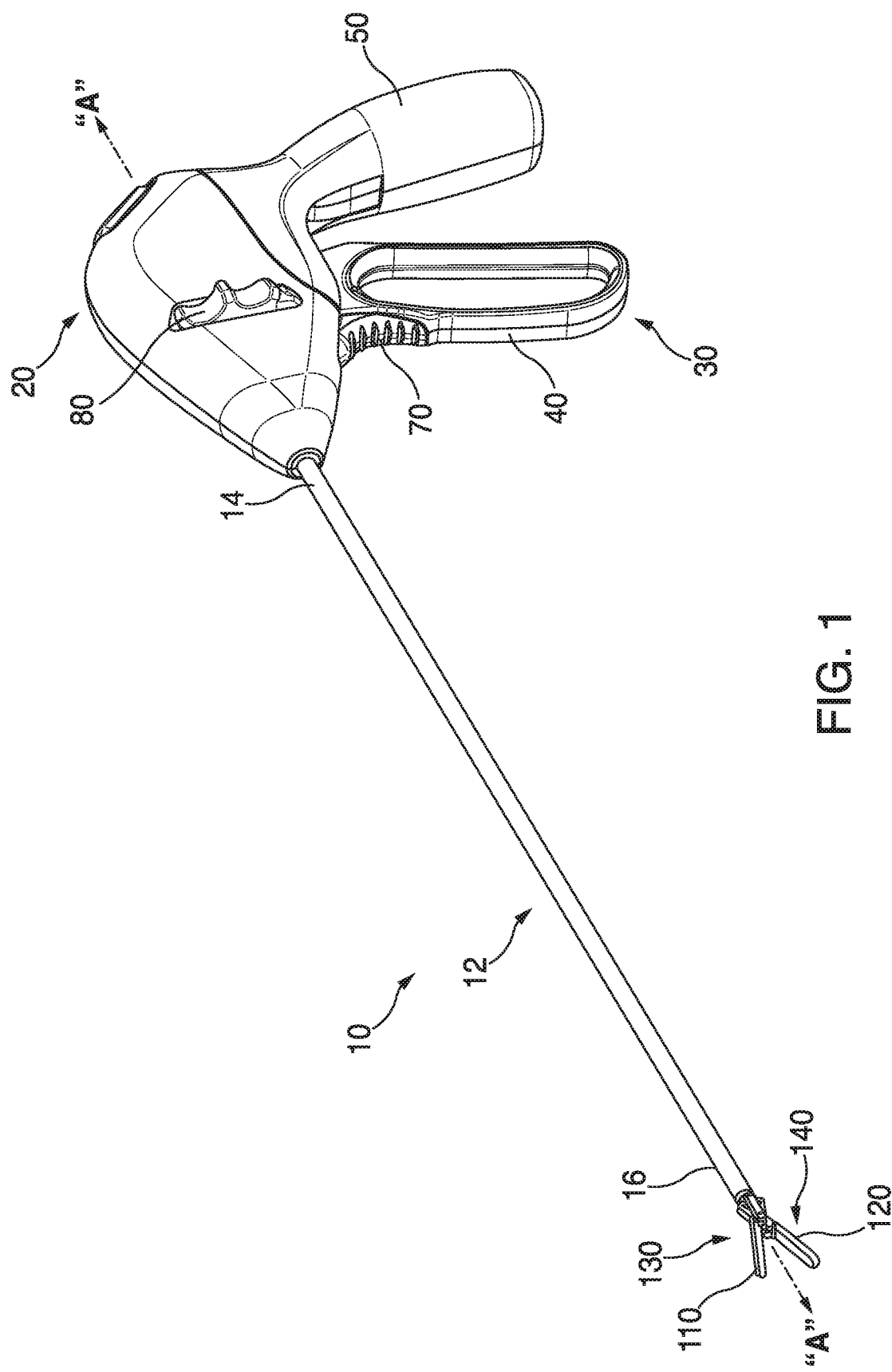
FIG. 1 is a perspective view of a laparoscopic bipolar forceps in accordance with an aspect of the present disclosure.

Particular aspects of the present electrosurgical tissue sealing instruments are described herein below with reference to the accompanying drawings; however, it is to be understood that the disclosed aspects are merely examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the concepts of the present disclosure in virtually any appropriately detailed structure.

Like reference numerals may refer to similar or identical elements throughout the description of the figures. As shown in the drawings and described throughout the following description, as is traditional when referring to relative positioning on a surgical instrument, the term "proximal" refers to the end of the apparatus which is closer to the user and the term "distal" refers to the end of the apparatus which is further away from the user. The term "clinician" refers to any medical professional (i.e., doctor, surgeon, nurse, or the like) performing a medical procedure involving the use of aspects described herein.

All numerical values and ranges disclosed above may vary by some amount. Whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Unless the meaning is clearly to the contrary, all ranges set forth herein are deemed to be inclusive of the endpoints. Unless specifically stated or obvious from context, as used herein, the term "about" when used in conjunction with a stated numerical value or range denotes somewhat more or somewhat less than the stated value or range, to within a range of ±10% of that stated value or range.

As described in more detail below with reference to the accompanying figures, the present disclosure is directed to electrosurgical instruments having a non-stick coating disposed on one or more components (e.g., tissue sealing plates, jaw members, electrical leads, insulators etc.) The thickness of the non-stick coating is carefully controlled, allowing for desired electrical performance while providing tissue sticking reduction during tissue sealing.

Any material capable of providing the desired functionality (namely, reduction of tissue sticking while simultaneously maintaining sufficient electrical transmission to permit tissue sealing) may be used as the non-stick coating, provided it has adequate biocompatibility. The material may be porous to allow for electrical transmission. Among such materials are silicone and silicone resins that can be applied using a plasma deposition process to precisely control thickness, and can withstand the heat generated during tissue sealing. Silicone resins suitable for the non-stick coating include, but are not limited to, polydimethyl siloxanes, polyester-modified methylphenyl polysiloxanes, such as polymethylsilane and polymethylsiloxane, and hydroxyl functional silicone resins. In some embodiments, the non-stick coating is made from a composition including a siloxane, which may include hexamethyldisiloxane, tetramethylsilane, hexamethyldisilazane, or combinations thereof.

In some embodiments, the non-stick coating is a polydimethylsiloxane coating formed by plasma-enhanced chemical vapor deposition ("PECVD") of hexamethyldisiloxane ("HMDSO"). Advantageously, the polydimethylsiloxane coating operates to reduce the sticking of tissue to the sealing plates and/or the entire jaw member. Additionally, the polydimethylsiloxane coating may operate to reduce the pitting of the sealing plates and may provide durability against electrical and/or mechanical degradation of the sealing plates and the jaw members, as a whole.

In some embodiments, opposing jaw members of an electrosurgical vessel sealing instrument (see FIGS. 1 and 2) include electrically conductive tissue sealing plates on which the non-stick coating is directly deposited. The application of the non-stick coating may be accomplished using any system and process capable of precisely controlling the thickness of the coating. In some embodiments, HMDSO is deposited on the sealing plates using plasma enhanced chemical vapor deposition (PECVD) or other suitable methods such as atmospheric pressure plasma enhanced chemical vapor deposition (AP-PECVD). For example, the application of the polydimethylsiloxane coating may be accomplished using a system and process that includes a plasma device coupled to a power source, a source of liquid and/or gas ionizable media (e.g., oxygen), a pump, and a vacuum chamber. One such illustrative system and process is described in commonly-owned U.S. Patent Application Publication No. US 2013/0116682, the entire contents of which are incorporated herein by reference. The power source may include any suitable components for delivering power or matching impedance to the plasma device. More particularly, the power source may be any radio frequency generator or other suitable power source capable of producing electrical power to ignite and sustain the ionizable media to generate a plasma effluent.

The thickness of the non-stick coating affects the non-stick performance of the sealing plates and may affect the tissue sealing performance of the sealing plates as well. For example, if the non-stick coating is too thick, the tissue sealing performance of the sealing plates may be negatively affected. More specifically, a non-stick coating above a particular thickness (e.g., greater than about 200 nm) may create a uniform dielectric barrier or surface impedance on the sealing plates, which may negatively impact the effectiveness of tissue sensing algorithms employed by an electrosurgical generator that controls the delivery of electrosurgical energy to the vessel sealing instrument based on sensed tissue parameters (e.g., impedance, temperature, etc.) generated by the application of electrosurgical energy to the tissue via the sealing plates. If the applied non-stick coating is too thin (e.g., less than about 20 nm), the non-stick coating may not provide adequate tissue sticking reduction.

Embodiments of the present disclosure provide for disposing a non-stick coating on components of a vessel sealing instrument (e.g., sealing plates, jaw members, electrical leads, insulators, etc.) at a particular thickness or within a particular range of thicknesses such that the non-stick coating provides adequate tissue sticking reduction during tissue sealing without negatively impacting tissue sealing performance of the vessel sealing instrument.

In some embodiments, a polydimethylsiloxane coating may be applied to a portion of the electrosurgical device at a thickness from about 20 nm to about 200 nm, in embodiments, the coating may be from about 25 nm to about 120 nm, and in further embodiments, from about 35 nm to about 85 nm. In a particular embodiment, the non-stick coating may be about 60 nm thick. In some embodiments, the thickness of the non-stick coating may vary such that the non-stick coating has a substantially non-uniform thickness. For example, a first portion of the non-stick coating may be about 60 nm thick and any one or more other portions of the non-stick coating may have a thickness other than about 60 nm but within the range of about 20 nm to about 200 nm, in embodiments within the range of from about 25 nm to about 120 nm, and in further embodiments, from about 35 nm to about 85 nm. In other embodiments, the non-stick coating has a substantially uniform thickness. Without wishing to be bound by any particular theory, it is believed that polydimethylsiloxane coatings in the foregoing range do not provide a complete surface seal, and that it is the lack of a complete uniform seal over the surface at these controlled thicknesses that allows the electrical algorithms of certain electrosurgical generators to perform properly. One such electrosurgical generator employing a tissue sensing algorithm is described in U.S. Pat. No. 9,603,752, the entire contents of which are incorporated herein by this reference. Those skilled in the art reviewing the present disclosure will readily envision other electrosurgical generators employing other algorithms.

In some embodiments, the thickness of the non-stick coating is about 0.01% of the thickness of the sealing plate.

Turning now to FIG. 1, an instrument generally identified as forceps 10 is for use with various surgical procedures and includes a housing 20, a handle assembly 30, a rotating assembly 80, a trigger assembly 70, and an end effector 130 that mutually cooperate to grasp, seal, and divide tubular vessels and vascular tissues. Forceps 10 includes a shaft 12 extending from a distal end of the housing 20. The shaft 12 has a distal end 16 configured to mechanically engage the end effector 130 and a proximal end 14 that mechanically engages the housing 20.

The end effector 130 includes opposing jaw members 110 and 120, which cooperate to effectively grasp tissue for sealing purposes. Both jaw members 110 and 120 pivot relative to one another about a pivot pin (not shown). Alternatively, the forceps 10 may include a jaw member 110 movable relative to a stationary jaw member 120, and vice versa. The jaw members 110 and 120 may be curved to facilitate manipulation of tissue and to provide better "line-of-sight" for accessing targeted tissues. A sensor 140 may be disposed on or proximate to at least one of the jaw members 110 and 120 for sensing tissue parameters (e.g., temperature, impedance, etc.) generated by the application of electrosurgical energy to tissue via the jaw members 110 and 120. The sensor 140 may include a temperature sensor, tissue hydration sensor, impedance sensor, optical clarity sensor, jaw gap sensor, strain and/or force sensor, or the like. Through a cable (not shown) coupling the forceps 10 to an electrosurgical generator (not shown), sensed tissue parameters may be transmitted as data to the electrosurgical generator having suitable data processing components (e.g., microcontroller, memory, sensor circuitry, etc.) for controlling delivery of electrosurgical energy to the forceps 10 based on data received from the sensor 140.

Examples of forceps are shown and described in U.S. Patent Application Publication No. 2013/0296922 and U.S. Pat. No. 9,655,673, the entire contents of each of which are incorporated herein by reference.

Figure 2:
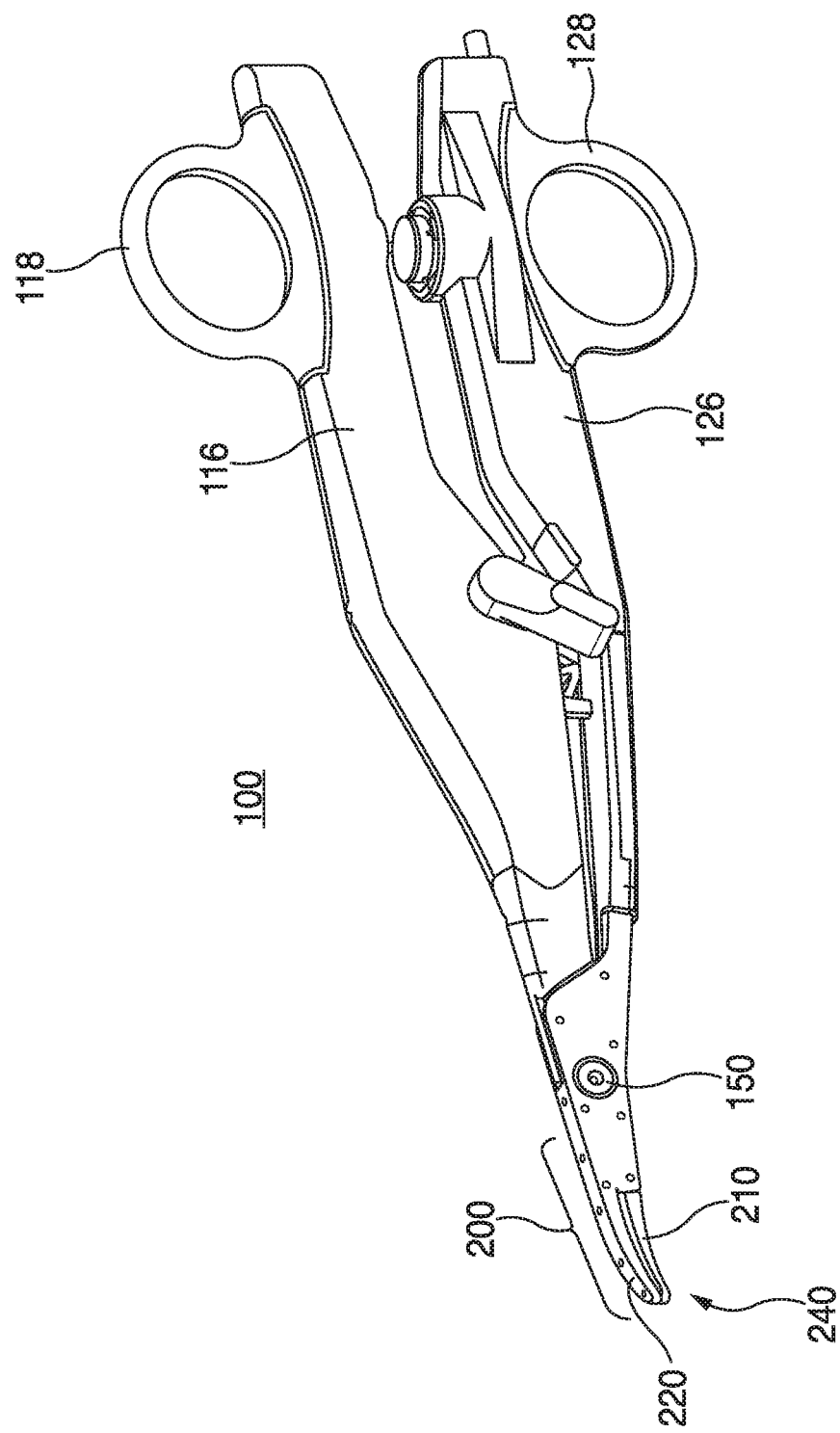
FIG. 2 is a perspective view of an open bipolar forceps according to an aspect of the present disclosure.

With regard to FIG. 2, an open forceps 100 for use with various surgical procedures is shown. The forceps 100 includes a pair of opposing shafts 116 and 126 having an end effector 200 disposed at a distal end of the shafts 116, 126. The end effector 200 includes pair of opposing jaw members 210 and 220 that are connected about a pivot member 150 and that are movable relative to one another to grasp tissue. Each shaft 116 and 126 includes a handle 118 and 128, respectively, to facilitate movement of the shafts 116 and 126 relative to one another to pivot the jaw members 210 and 220 between an open position, wherein the jaw members 210 and 220 are disposed in spaced relation relative to one another, and a closed position, wherein the jaw members 210 and 220 cooperate to grasp tissue there between. Similar to the forceps 10 shown in FIG. 1, a sensor 240 may be disposed on or proximate to at least one of the jaw members 210 and 220 of the forceps 100 for sensing tissue parameters (e.g., temperature, impedance, etc.) generated by the application of electrosurgical energy to tissue via the jaw members 210 and 220. The sensor 240 may include a temperature sensor, tissue hydration sensor, impedance sensor, optical clarity sensor, or the like. Through a cable (not shown) coupling the forceps 100 to an electrosurgical generator (not shown), sensed tissue parameters may be transmitted as data to the electrosurgical generator having suitable data processing components (e.g., microcontroller, memory, sensor circuitry, etc.) for controlling delivery of electrosurgical energy to the forceps 100 based on data received from the sensor 240.

Figure 3A:
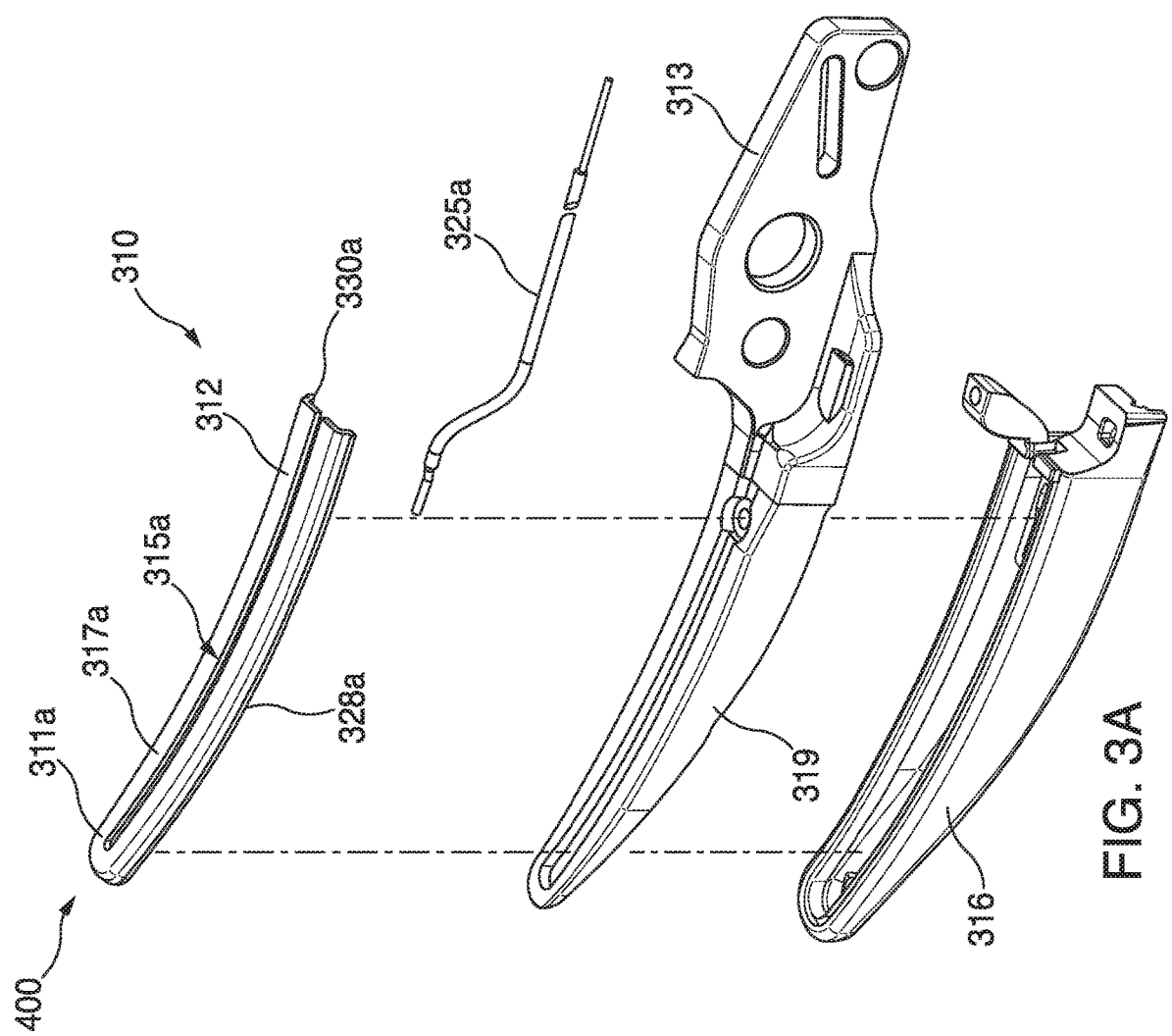
FIGS. 3A and 3B are exploded views of opposing jaw members according to an aspect of the present disclosure.
Figure 3B:
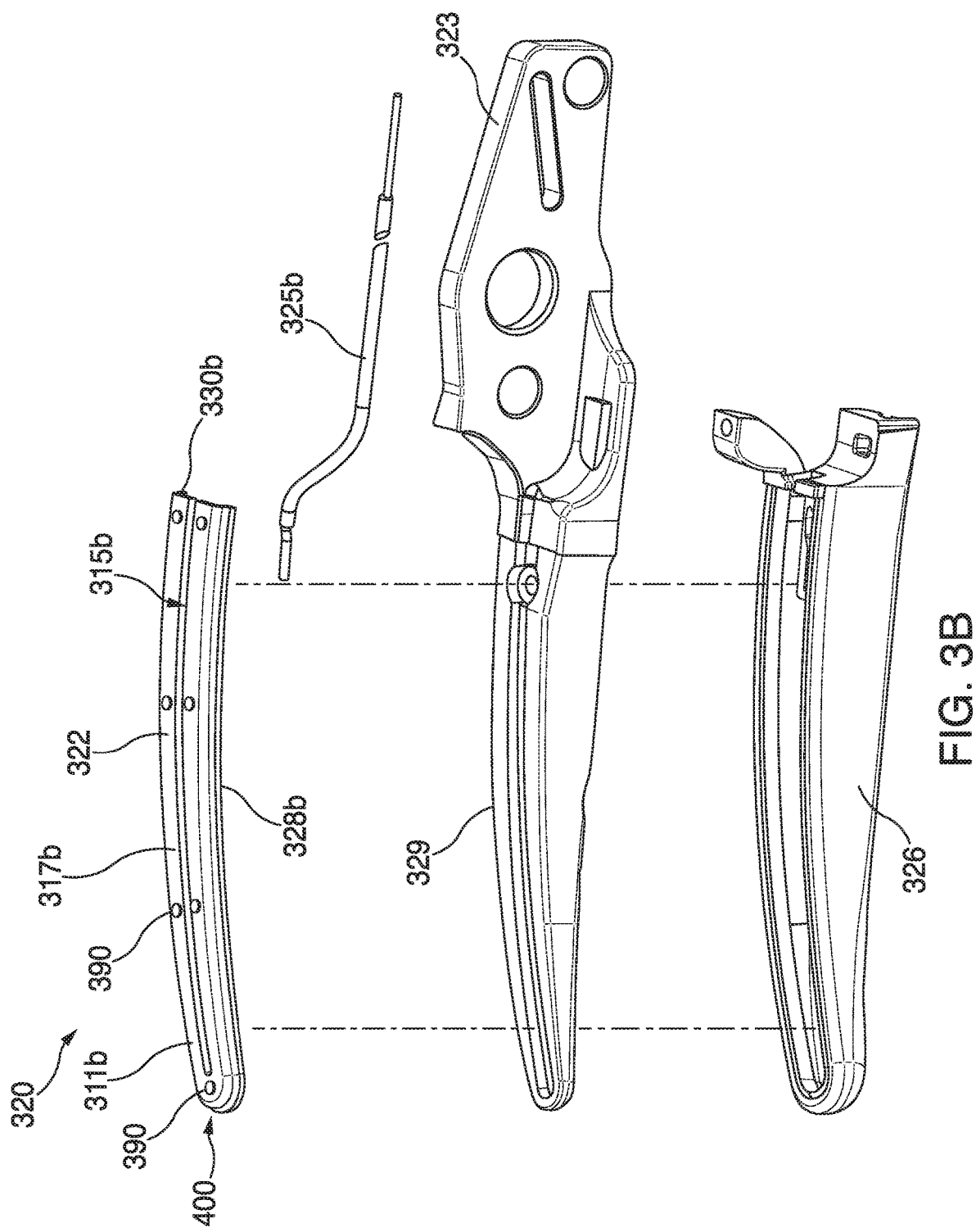

FIGS. 3A and 3B show perspective views of the jaw members 310 and 320, respectively, according to an embodiment of the present disclosure. The jaw members 310 and 320 may be utilized with the endoscopic forceps 10 (FIG. 1) or the open forceps 100 (FIG. 2) and operate similarly as described above with respect to the jaw members 110 and 120 (FIG. 1) and the jaw members 210 and 220 (FIG. 2). Each of the jaw members 310 and 320 include: sealing plates 312 and 322, respectively; electrical leads 325a and 325b, respectively; and support bases 319 and 329 that extend distally from flanges 313 and 323, respectively.

Each of the sealing plates 312 and 322 include an underside 328a and 328b, respectively, that may include a respective electrically insulative layer 330a and 330b bonded thereto or otherwise disposed thereon. The electrically insulative layers 330a and 330b operate to electrically insulate the sealing plates 312 and 322, respectively, from the support bases 319 and 329, respectively. Further, the electrically insulative layers 330a and 330b operate to prevent or slow the onset of corrosion of the sealing plates 312 and 322, respectively, at least on the undersides 328a, 328b thereof. In one embodiment, the electrically insulative layers 330a and 330b may be formed from polyimide. However, in other embodiments, any suitable electrically insulative material may be utilized, such as polycarbonate, polyethylene, etc.

Additionally, each of the jaw members 310 and 320 include an outer surface 311a and 311b, respectively, that includes a non-stick (e.g., polydimethylsiloxane) coating 400 disposed thereon. The non-stick coating 400 may be disposed on selective portions of either of the jaw members 310 and 320, or may be disposed on the entire outer surfaces 311a and 311b. In some embodiments, the non-stick coating 400 is disposed on a tissue-engaging surface 317a and 317b of the sealing plates 312 and 322, respectively. The non-stick coating 400 operates to reduce the sticking of tissue to the sealing plates 312 and 322, the jaw members 310 and 320, the electrical leads 325a and 325b, and/or the surrounding insulating material.

The support bases 319 and 329 are configured to support the sealing plates 312 and 322 thereon. The sealing plates 312 and 322 may be affixed atop the support bases 319 and 329, respectively, by any suitable method including but not limited to snap-fitting, overmolding, stamping, ultrasonic welding, laser welding, etc. The support bases 319 and 329 and the sealing plates 312 and 322 are at least partially encapsulated by insulative housings 316 and 326, respectively, by way of an overmolding process to secure sealing plates 312 and 322 to support bases 319 and 329, respectively. The sealing plates 312 and 322 are coupled to electrical leads 325a and 325b, respectively, via any suitable method (e.g., ultrasonic welding, crimping, soldering, etc.). The electrical leads 325a and 325b serve to deliver electrosurgical energy (e.g., from an electrosurgical energy generator) to the sealing plates 312 and 322, respectively. More specifically, electrical lead 325a supplies a first electrical potential to sealing plate 312 and electrical lead 325b supplies a second electrical potential to opposing sealing plate 322.

Jaw member 320 (and/or jaw member 310) may also include a series of stop members 390 disposed on the tissue-engaging surface 311b of the sealing plate 322 to facilitate gripping and manipulation of tissue and to define a gap between the jaw members 310 and 320 during sealing and cutting of tissue. The series of stop members 390 may be disposed (e.g., formed, deposited, sprayed, affixed, coupled, etc.) onto the sealing plate 322 during manufacturing. Some or all of the stop members 390 may be coated with the non-stick coating 400 or, alternatively, may be disposed on top of the non-stick coating 400.

The sealing plates 312 and 322 may include longitudinal knife slots 315a and 315b, respectively, defined there through and configured to receive a knife blade (not shown) that reciprocates through the knife slots 315a and 315b to cut tissue. The electrically insulative layers 330a and 330b disposed on the respective undersides 328a and 328b of sealing plates 312 and 322, respectively, allow for various blade configurations such as, for example, T-shaped blades or I-shaped blades that may contact the underside of the sealing plate (and/or insulating layer) during reciprocation through knife slots 315a, 315b. That is, the electrically insulative layers 330a, 330b operate to protect both the knife blade and the undersides 328a and 328b of the sealing plates 312 and 322, respectively, from damage or wearing. Further, in the instance that an electrically conductive knife blade is utilized (e.g., for electric tissue cutting), the electrically insulative layers 330a, 330b help to electrically insulate the sealing plates 312, 322 from the electrically conductive knife blade.

Figure 4A:
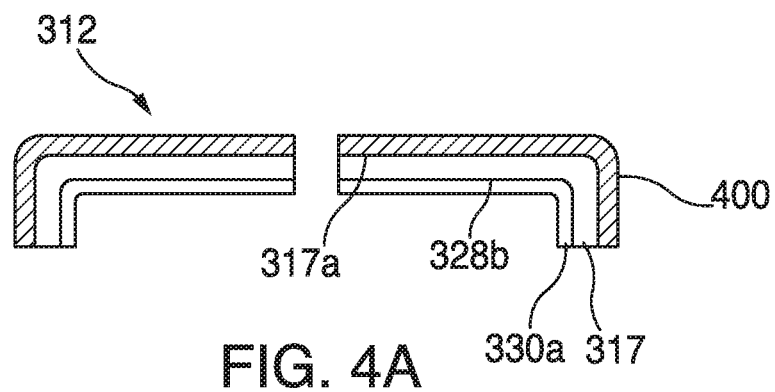
FIG. 4A is a front cross sectional view of a sealing plate according to an aspect of the present disclosure.

Turning now to FIG. 4A, a front cross sectional view of sealing plate 312 is shown and will be described. Sealing plate 312 has a stainless steel layer 317, a non-stick coating 400, and, optionally, an electrically insulative layer 330a disposed on the underside 328b of the stainless steel layer 317. The non-stick coating 400 may be applied to at least the outer surface 311a of the stainless steel layer 317. Bonding electrically insulative layer 330a to stainless steel layer 317 may be accomplished by any suitable method including, but not limited to, applying adhesive between electrically insulative layer 330a and stainless steel layer 317, using heat treatment to bond electrically insulative layer 330a to stainless steel layer 317, and/or any combinations thereof. The optional electrically insulative layer 330a may have a thickness ranging from about 0.0005 inches to about 0.01 inches.

The non-stick coating 400 may be discontinuous or continuous. In some embodiments, the discontinuity or continuity of the non-stick coating 400 may depend on the thickness of the non-stick coating 400. In some embodiments, the non-stick coating may be continuous over the entire sealing plate 312, thereby hermetically sealing the sealing plate 312. In some embodiments, the non-stick coating may be discontinuous over the entire sealing plate 312. The discontinuous non-stick coating may be applied intermittently on the sealing plate 312 using a suitable discontinuous-coating or patch-coating process. The patchiness of the discontinuous non-stick coating may allow the thickness of the discontinuous non-stick coating to be increased relative to a continuous non-stick coating while maintaining adequate non-stick performance and tissue sealing performance.

In some embodiments, the sealing plate 312 may be formed by bonding a sheet of electrically insulative material to a sheet of stainless steel and coating the sheet of stainless steel with a non-stick coating. Once the two materials are bonded together, and the stainless steel sheet is coated with the non-stick coating 400, sealing plate 312 may be formed by stamping, machining, or any other suitable method used to form a sealing plate.

In some embodiments, the sealing plate 312 may first be formed by stamping, machining, or any other suitable method used to form a sealing plate. Once the sealing plate 312 is formed, the non-stick coating 400 is applied to the sealing plate 312 prior to assembling jaw member 310. Once the sealing plate 312 is coated with the non-stick coating 400, the sealing plate 312 may be affixed atop the support base 319, secured to the support base 319 via the insulative housing 316, and coupled to the electrical lead 325a as described above with respect to FIG. 3A to form the jaw member 310. Optionally, once the jaw member 310 is formed, a non-stick coating may be applied to the other components of the jaw member 310 (e.g., the support base 319, the insulative housing 316, the electrical lead 325a, etc.). In some embodiments, a non-stick coating may be applied to other components of forceps 10 (FIG. 1) or forceps 100 (FIG. 2) to reduce frictional sticking associated with operation of these devices. For example, a non-stick coating may be applied to the shaft 12 of forceps 10, to the pivot member 150 and opposing shafts 116 and 126 of forceps 100, and/or to a knife (not shown) used with either of forceps 10 or forceps 100.

Figure 4B:
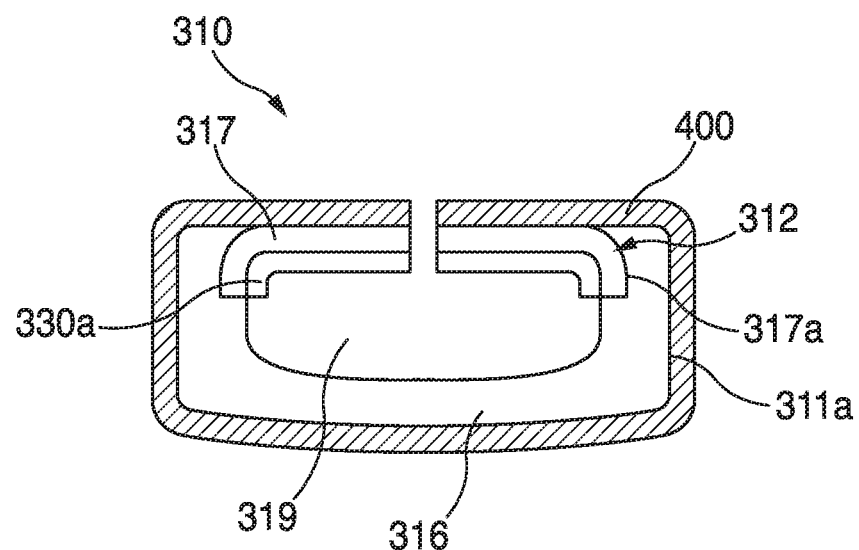
FIG. 4B is a front cross sectional view of a jaw member according to an aspect of the present disclosure.

Turning now to FIG. 4B, a front cross sectional view of jaw member 310 is shown and will be described. Jaw member 310 includes sealing plate 312 having a stainless steel layer 317 and, optionally, an electrically insulative layer 330a. Sealing plate 312 is affixed to support base 319 via any suitable process. Additionally, with sealing plate 312 secured to support base 319, the combined sealing plate 312 and support base 319 is secured to insulative housing 316 via any suitable process. A non-stick coating 400 is applied to the outer surface 311a of the assembled sealing plate 312, the support base 319, the insulative housing 316, and, optionally the electrical lead 325a (FIG. 3A). In some embodiments it may be useful to partially coat the outer surface 311a of the jaw member 310 or include thicker layers of the non-stick coating 400 on different portions of the outer surface 311a of the jaw member 310.

Additionally or alternatively, in some embodiments, the sealing plate 312 may be coated with the non-stick coating 400 in the manner described above with respect to FIG. 4A and the outer surface 311a of the jaw member 310 may also be coated with the non-stick coating 400.

Once the non-stick coating 400 is disposed on the sealing plates 312 and 322 and/or the jaw member 310, which may be assembled with an opposing jaw member (e.g., pivotably coupled) to form an end effector (e.g., end effector 130 or end effector 200). In some embodiments, the non-stick coating 400 may be disposed on the sealing plates 312 and 322 and/or the jaw member 310 subsequent to assembly of the end effector.

In some embodiments, a polydimethylsiloxane coating at the above-described thickness or within the above-described range of thicknesses may be combined with one or more additional coatings. For example, the one or more coatings may be disposed directly on the stainless steel layer of the sealing plate prior to the polydimethylsiloxane coating being deposited such that the polydimethylsiloxane coating is disposed directly on the one or more coatings and not directly on the stainless steel layer of the sealing plate. U.S. Publication No. 2017/0119457 describes a vessel sealing instrument having sealing plates with a HMDSO-based coating disposed over a chromium nitride ("CrN") coating.

It is envisioned that any suitable chemical vapor deposition or plasma vacuum system may be used to perform the method, such as the system disclosed in U.S. Pat. No. 8,187,484, the entire contents of which is incorporated by reference herein. The non-stick coating 400 may be applied using the method disclosed in U.S. patent application Ser. No. 16/059,279, the entire contents of which is incorporated by reference herein.

Figure 5:
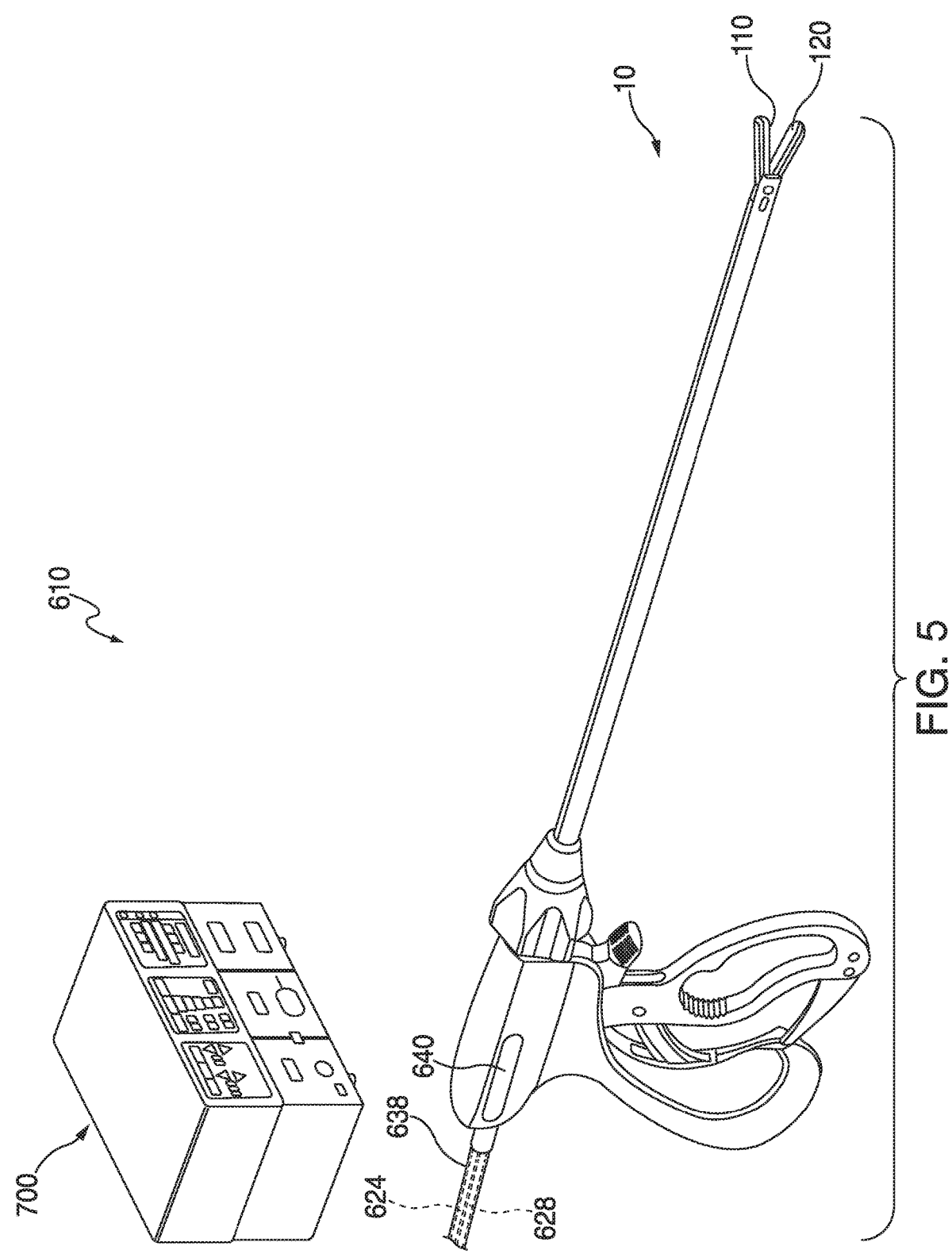
FIG. 5 is a perspective view of an electrosurgical system according to an aspect of the present disclosure.

FIG. 5 is a perspective view of the components of one illustrative embodiment of an electrosurgical system 610 according to the present disclosure. The system 610 may include an electrosurgical generator 700 configured to couple to the forceps 10 (FIG. 1), forceps 100 (FIG. 2), or any other suitable electrosurgical instrument. One of the jaw members 110 or 120 of the forceps 10 acts as an active electrode with the other jaw member being a return electrode. Electrosurgical alternating RF current is supplied to the active electrode of the forceps 10 by a generator 700 via a supply line 624 that is connected to an active terminal 730 (FIG. 5) of the generator 700. The alternating RF current is returned to the generator 700 from the return electrode via a return line 628 at a return terminal 632 (FIG. 5) of the generator 700. The supply line 624 and the return line 628 may be enclosed in a cable 638

The forceps 10 may be coupled to the generator 700 at a port having connections to the active and return terminals 730 and 732 (e.g., pins) via a plug (not shown) disposed at the end of the cable 638, wherein the plug includes contacts from the supply and return lines 624, 628 as described in more detail below.

Figure 6:
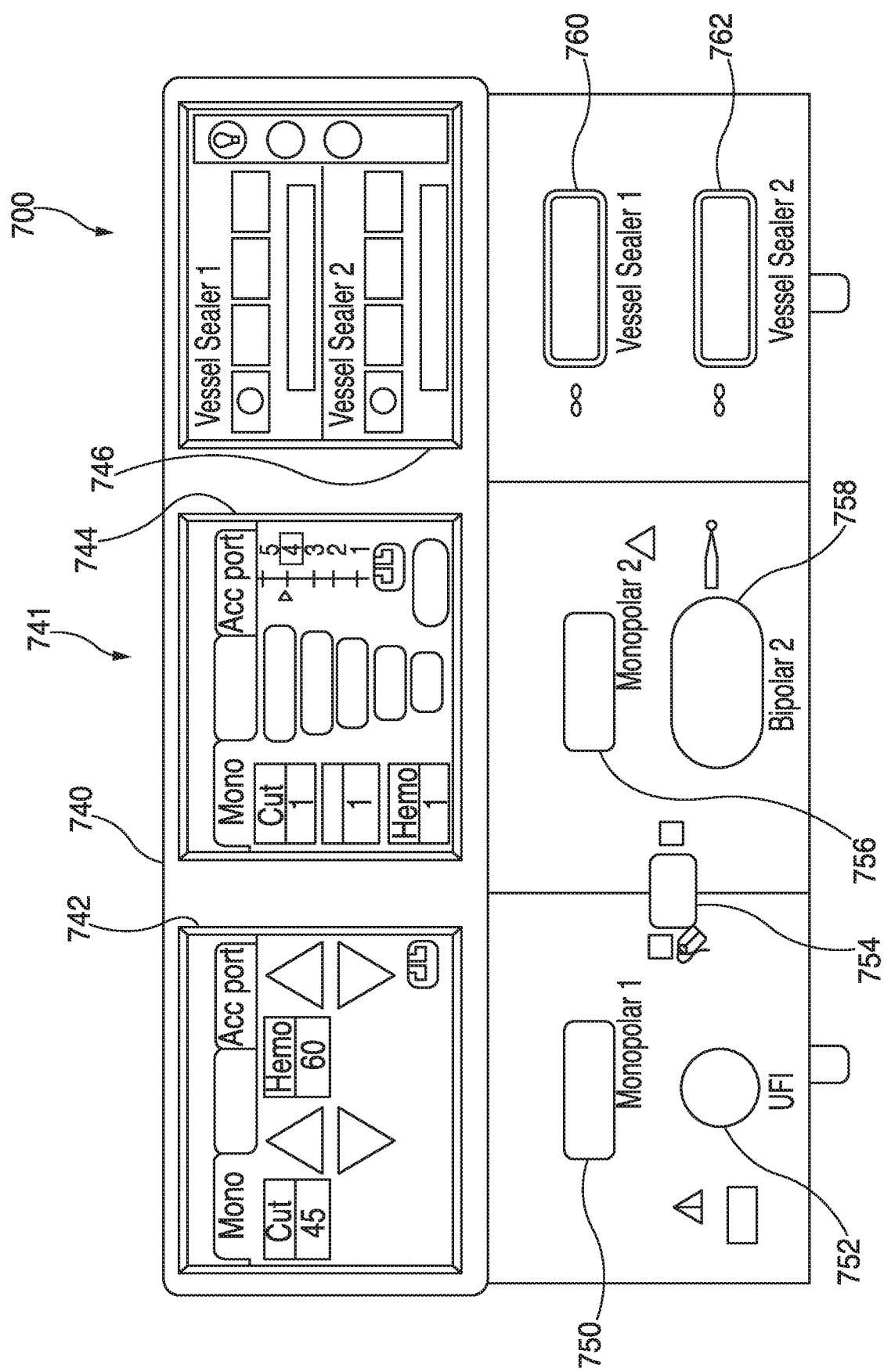
FIG. 6 is a front view of an electrosurgical generator of the electrosurgical system of FIG. 5 according to an aspect of the present disclosure.

With reference to FIG. 6, a front face 740 of the generator 700 is shown. The generator 700 may include a plurality of ports 750-762 to accommodate various types of electrosurgical instruments (e.g., monopolar electrosurgical instrument, forceps 10, forceps 100, etc.).

The generator 700 includes a user interface 741 having one or more display screens 742, 744, 746 for providing the user with variety of output information (e.g., intensity settings, treatment complete indicators, etc.). Each of the screens 742, 744, 746 is associated with a corresponding port 750-762. The generator 700 includes suitable input controls (e.g., buttons, activators, switches, touch screen, etc.) for controlling the generator 700. The screens 742, 744, 746 are also configured as touch screens that display a corresponding menu for the instruments (e.g., forceps 10). The user then adjusts inputs by simply touching corresponding menu options.

Screen 642 controls monopolar output and the devices connected to the ports 750 and 752. Port 750 is configured to couple to a monopolar electrosurgical instrument and port 752 is configured to couple to a foot switch (not shown). The foot switch may be used to provide for additional inputs (e.g., replicating inputs of the generator 700). Screen 744 controls monopolar and bipolar output and the devices connected to the ports 756 and 758. Port 756 is configured to couple to other monopolar instruments. Port 758 is configured to couple to a bipolar instrument (not shown).

Screen 746 controls the forceps 10 that may be plugged into one of the ports 760 and 762, respectively. The generator 700 outputs energy through the ports 760 and 762 suitable for sealing tissue grasped by the forceps 10. In particular, screen 746 outputs a user interface that allows the user to input a user-defined intensity setting for each of the ports 760 and 762. The user-defined setting may be any setting that allows the user to adjust one or more energy delivery parameters, such as power, current, voltage, energy, etc. or sealing parameters, such as energy rate limiters, sealing duration, etc. The user-defined setting is transmitted to a controller 724 (FIG. 7) where the setting may be saved in memory. In embodiments, the intensity setting may be a number scale, such as for example, from one to ten or one to five. In embodiments, the intensity setting may be associated with an output curve of the generator 700. The intensity settings may be specific for each forceps 10 being utilized, such that various instruments provide the user with a specific intensity scale corresponding to the forceps 10. The active and return terminals 730 and 732 (FIG. 7) may be coupled to any of the desired ports 750-762.

With continued reference to FIG. 6, each of the ports 750-762 may include a reader, such as an optical reader or a radio frequency interrogator, configured to communicate with the forceps 10 to extract data pertaining to the forceps 10. Such data may be encoded in a barcode, an RFID tag, computer-readable storage, or any other data storage medium 640, which may be disposed on the forceps 10 or any of its components, such as the cable 638. In embodiments, the data may include whether the forceps 10 includes coated or uncoated jaw members 110 and 120. In further embodiments, the data may also include properties of the coating, such as its thickness, dielectric properties, current and voltage limits, temperature limits, and the like.

Figure 7:
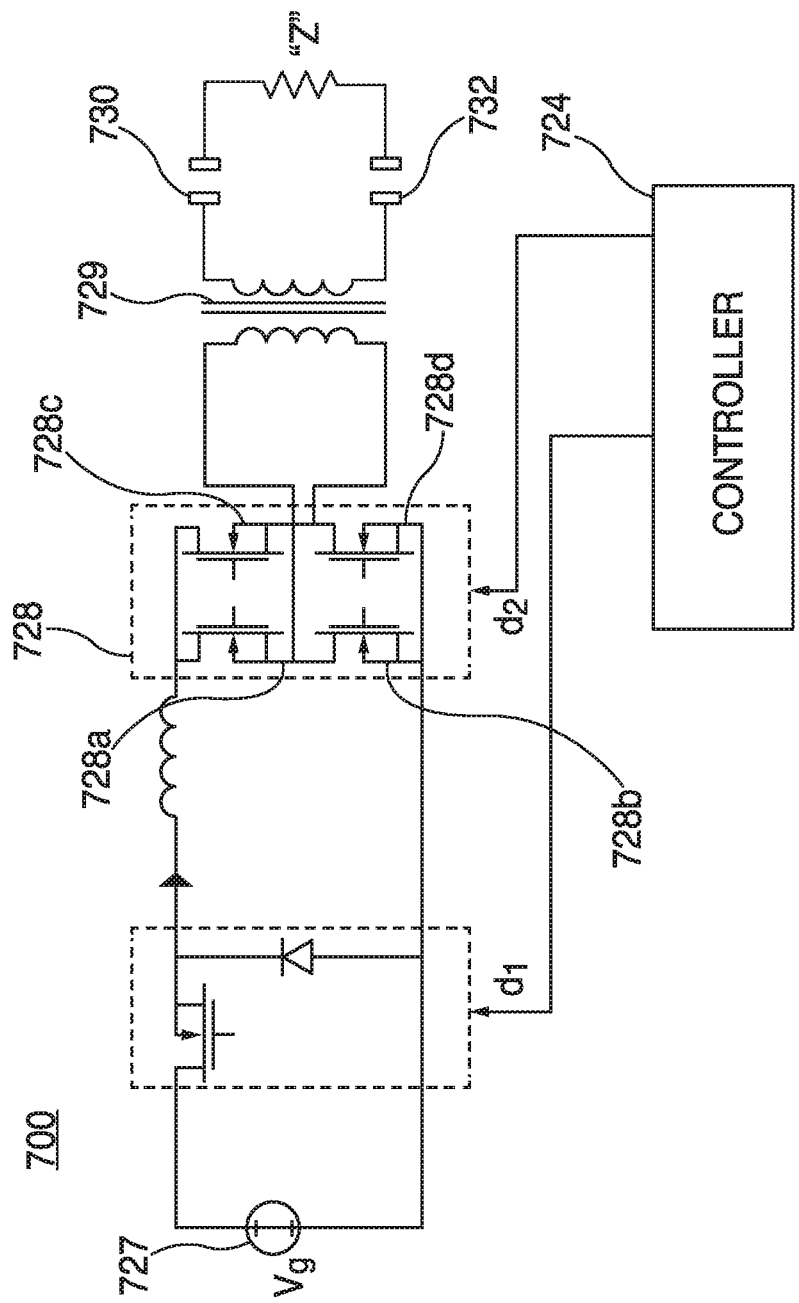
FIG. 7 is a schematic diagram of the electrosurgical generator according to an aspect of the present disclosure.

FIG. 7 shows a schematic block diagram of the generator 700, which includes a controller 724, a power supply 727, and a power converter 728. The power supply 727 may be a high voltage, DC power supply connected to an AC source (e.g., line voltage) and provides high voltage, DC power to the power converter 728, which then converts high voltage, DC power into RF energy and delivers the energy to the active terminal 730. The energy is returned thereto via the return terminal 732. The active and return terminals 730 and 732 are coupled to the power converter 728 through an isolation transformer 729.

The power converter 728 is configured to operate in a plurality of modes, during which the generator 700 outputs corresponding waveforms having specific duty cycles, peak voltages, crest factors, etc. It is envisioned that in other embodiments, the generator 700 may be based on other types of suitable power supply topologies. Power converter 728 may be a resonant RF amplifier or a non-resonant RF amplifier, as shown. A non-resonant RF amplifier, as used herein, denotes an amplifier lacking any tuning components, i.e., inductors, capacitors, etc., disposed between the power converter and a load "Z," e.g., tissue coupled through forceps 10.

The controller 724 includes a processor (not shown) operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by any logic control circuit adapted to perform the calculations and/or execute a set of instructions described herein.

The controller 724 includes an output port that is operably connected to the power supply 727 and/or power converter 728 allowing the processor to control the output of the generator 700 according to either open and/or closed control loop schemes. A closed loop control scheme is a feedback control loop, in which a plurality of sensors measure a variety of tissue and energy properties (e.g., tissue impedance, tissue temperature, output power, current and/or voltage, etc.), and provide feedback to the controller 724. The controller 724 then controls the power supply 727 and/or power converter 728, which adjusts the DC and/or power supply, respectively.

The generator 700 according to the present disclosure may also include a plurality of sensors (not shown). The sensors may be coupled to the power supply 727 and/or power converter 728 and may be configured to sense properties of DC current supplied to the power converter 728 and/or RF energy outputted by the power converter 728, respectively. The controller 724 also receives input signals from the input controls of the generator 700 and/or forceps 10. The controller 724 utilizes the input signals to adjust power outputted by the generator 700 and/or performs other control functions thereon.

Power converter 728 includes a plurality of switching elements 728a-728d arranged in an H-bridge topology. In embodiments, power converter 728 may be configured according to any suitable topology including, but not limited to, half-bridge, full-bridge, push-pull, and the like. Suitable switching elements include voltage-controlled devices such as transistors, field-effect transistors (FETs), combinations thereof, and the like. In embodiments, the FETs may be formed from gallium nitride, aluminum nitride, boron nitride, silicon carbide, or any other suitable wide bandgap materials. In further embodiments, the FETs may be any suitable FETs, such as conventional silicon FETs.

The controller 724 is in communication with both power supply 727 and power converter 728. Controller 724 is configured to output control signals, which may be a pulse-width modulated ("PWM") signal, to switching elements 728a-728d as described in further detail in application published as U.S. Patent Application Publication No. 2014/0254221, the entire contents of which are incorporated by reference herein. In particular, controller 724 is configured to modulate a control signal $d_1$ supplied to power supply 727 and control signal $d_2$ supplied to switching elements 728a-728d of power converter 728. Additionally, controller 724 is configured to calculate power characteristics of generator 700, and control generator 700 based at least in part on the measured power characteristics.

The controller 724 is configured to execute one or more vessel sealing algorithms, which control the output of the generator 700 to treat tissue (e.g., seal vessels). Exemplary algorithms are disclosed in commonly-owned U.S. Pat. No. 8,147,485 and U.S. Patent Application Publication No. 2016/0045248, the entire disclosures of all of which are incorporated by reference herein.

Algorithms according to the present disclosure may be embodied as software instructions executable by the controller 724. In embodiments, an algorithm may be an impedance-based energy delivery algorithm in which energy is delivered by the generator 700 to the tissue until a predetermined impedance threshold is met or energy is otherwise delivered based on measured tissue impedance. In further embodiments, the sealing algorithm may include configurable parameters, which may be a value settable manually by the user or automatically by the controller 724 during or prior to execution of the sealing algorithms. Suitable configurable parameters include threshold values, such as completion impedance, starting impedance, and offset impedance; intensity setting, such as a current setting, and a voltage setting; and duration setting, such as maximum time of energy application. In embodiments, other parameters of the algorithms may also be adjusted, such as the parameters of algorithms disclosed in U.S. Pat. No. 8,147,485 and U.S. Patent Application Publication No. 2016/0045248, which are incorporated by reference as stated above.

In embodiments, the non-stick coating 400 of the jaw members 110 and 120 may be too thick and thus, too insulating, such that the measured impedance between the jaw members 110 and 120 would be too high for the generator 700 to output RF energy to treat tissue, such as seal vessels. The present disclosure provides for a plurality of algorithms executable by the controller 724, which are configured to apply a sufficient amount of energy to the jaw members 110 and 120 to achieve conductor breakthrough in order to overcome excessive insulation of the non-stick coating 400 in situations, such as when the non-stick coating 400 is too thick.

The present disclosure provides for pre-treatment algorithms embodied as software instructions, which when executable by the controller 724, which controls the power converter 728 to output an RF waveform for overcoming excessing insulation of the non-stick coating 400 and achieve conductor breakthrough. The generator 700 monitors one or more parameters that are indicative of conductor breakthrough. Once the controller 724 determines that conductor breakthrough has occurred, the controller 724 proceeds to execute a tissue treatment algorithm. If the conductor breakthrough is not achieved, the controller 724 prevents the generator 700 from outputting energy.

Figure 8:
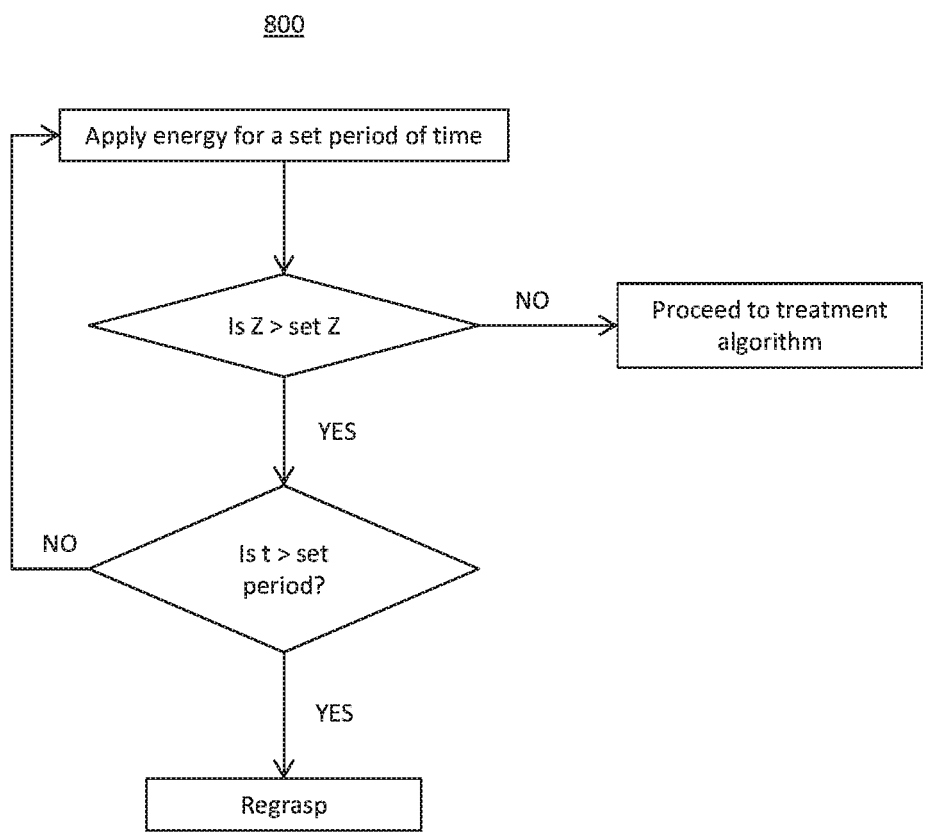
FIG. 8 is a flow chart of a method for applying a radio frequency waveform to achieve conductor breakthrough through a dielectric coating according to an aspect of the present disclosure.

With reference to FIG. 8, a pre-treatment algorithm for achieving conductor breakthrough in jaw members 110 and 120 or any other electrodes having the non-stick coating 400 is embodied as a flow chart 800. Initially, the controller 724 signals the power converter 728 to output an RF waveform. The RF waveform may be a 100% duty cycle continuous waveform having maximum power of about 300 Watts, maximum current of about 3 Amps, and maximum voltage of about 200 Volts. In further embodiments, the RF waveform may be a pulsed waveform having a duty cycle from about 25% to about 90%. The RF waveform is applied for a set period of time, which may be from about 50 msec to about 1 sec, and in embodiments, may be from about 100 msec to about 200 msec. The controller 724 continuously receives measured impedance from one or more sensors (not shown) of the generator 700 and compares the measured impedance to a set impedance that is indicative of achieving conductor breakthrough of the non-stick coating 400. The set impedance may be settable by the user or automatically by the generator 700 based on the type of forceps 10 that is connected to the generator 700.

If the measured impedance drops below the set impedance, then the controller 724 proceeds to execute a treatment algorithm such as sealing algorithms disclosed in U.S. Pat. No. 8,147,485 and U.S. Patent Application Publication No. 2016/0045248, which are incorporated by reference above. If the impedance is above the set threshold, then the generator 700 continues to apply the RF waveform until a predetermined time limit is reached.

In embodiments, the threshold for switching to the treatment algorithm may be any other parameter, such as voltage or current. With respect to other parameters the threshold is selected that is also indicative of increasing conductivity of the jaw members 110 and 120. Increasing conductivity corresponds to achieving conductor breakthrough. Thus, in embodiments where current and/or voltage is used as a parameter, the controller 724 compares the measured current and/or voltage to a set current and/or voltage threshold to determine if the measured current and/or voltage is below the set current threshold. Once the measured current and/or voltage exceeds the set current threshold, then the controller 724 proceeds to execute the treatment algorithm. Similarly to the impedance being used as a parameter, the generator 700 continues to apply the RF waveform until the set time period expires.

The controller 724 maintains a timer for the application of the RF waveform and compares the measured time of the timer to the set time period. In embodiments, the timer may be maintained by any other controller within or outside the generator 700. If the timer has not yet expired and the impedance does not drop below the set threshold (or if current and/or voltage does not exceed the set threshold), the generator 700 continues to apply the RF waveform until set time period expires. If the set time period expires without the measured impedance dropping below the set threshold, or without the measured current and/or voltage exceeding the set threshold, then the pre-treatment algorithm instructs the generator 700 to issue a retry alert, such as instructing the user to re-grasp the tissue with the jaw members 110 and 120.

Figure 9:
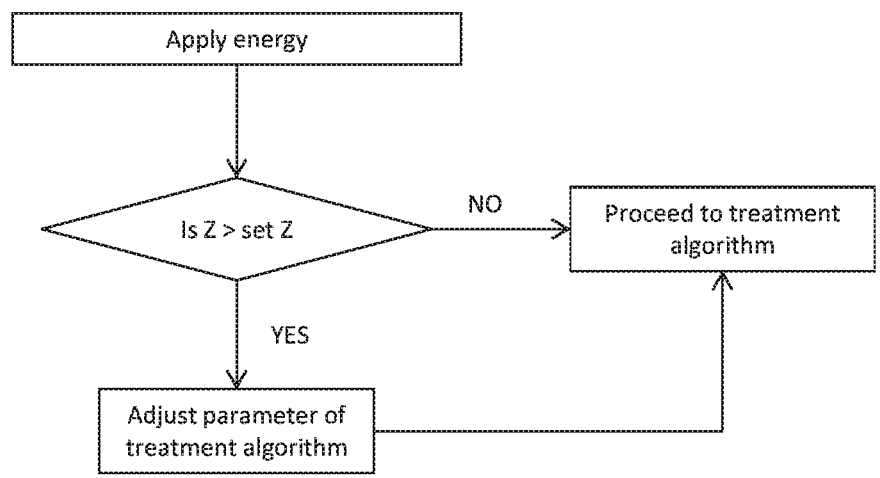
FIG. 9 is a flow chart of a method for applying a radio frequency waveform to achieve conductor breakthrough through a dielectric coating according to another aspect of the present disclosure.

With reference to FIG. 9, another embodiment of a pre-treatment algorithm for achieving conductor breakthrough in the non-stick coating 400 is shown as a flow chart 900. Initially, the controller 724 signals the power converter 728 to output the RF waveform, which may be the same as the RF waveform of the algorithm of the flow chart 800. The RF waveform may be applied for a period of time, which may be from about 1 msec to about 1 sec, and in embodiments, may be from about 100 msec to about 200 msec. The controller 724 continuously receives measured impedance from sensors of the generator 700 and compares the measured impedance to the set impedance that is indicative of achieving conductor breakthrough of the non-stick coating 400. In embodiments, the controller 724 may sample the measured impedance at a predetermined rate. The set impedance may be settable by the user or automatically by the generator 700 based on the type of forceps 10 connected to the generator 700. Similarly to the algorithm of the flow chart 800, the measured parameter and threshold may be voltage and/or current.

If the measured impedance drops below the set impedance or if the measured parameter is voltage and/or current and exceeds the set threshold, then the controller 724 proceeds to execute the treatment algorithm such as sealing algorithms disclosed in U.S. Pat. No. 8,147,485 and U.S. Patent Application Publication No. 2016/0045248, which are incorporated by reference above. If the impedance is above the set threshold, then the generator 700 executes the treatment algorithm, but with an adjustment.

In embodiments, the treatment algorithm may include a plurality of power settings corresponding to the power of the treatment effect. Thus, a low setting, e.g., setting of 1, corresponds to the lowest power setting, and a high power setting, e.g., setting of 5, corresponds to the highest power setting. The power setting may be implemented in the algorithm by associating a power setting value with one or more adjustable parameters within the algorithm. In embodiments, adjustable parameters of the algorithm may include a current setting and a voltage setting at which the algorithm, when executed by the controller 724 outputs a treatment RF waveform. In embodiments, the controller 724 may store a look-up table of power setting values and one or more corresponding adjustable parameters, such that when the power setting is selected, the controller 724 selects corresponding parameters.

The adjustment to the treatment algorithm includes automatically selecting a suitable power setting based on the comparison of the measured impedance or other parameter to the set threshold. If the impedance is above the set threshold, then the generator 700 executes the treatment algorithm at a higher power setting.

In embodiments, the controller 724 is configured to execute the treatment algorithm at a higher power setting if the impedance is above the set threshold. The amount of the power increase is correlated to the amount of the difference between the measured impedance or other parameter and the set threshold. In further embodiments, the algorithm may adjust the power setting of the treatment algorithm if the measured impedance is also below the set threshold. Thus, if the measured impedance is substantially equal (±5%) to the set threshold, then the controller 724 proceeds to execute the pre-treatment algorithm without modifying the power setting. However, if the measured impedance is different from the set threshold, then the controller 724 executes the pre-treatment algorithm by adjusting the power setting by an adjustment value, which may be the same as a percentage difference between the measured parameter and the set threshold. In embodiments, the adjustment value may be based on a look-up table or calculated according to a transfer function by the controller 724.

Figure 10:
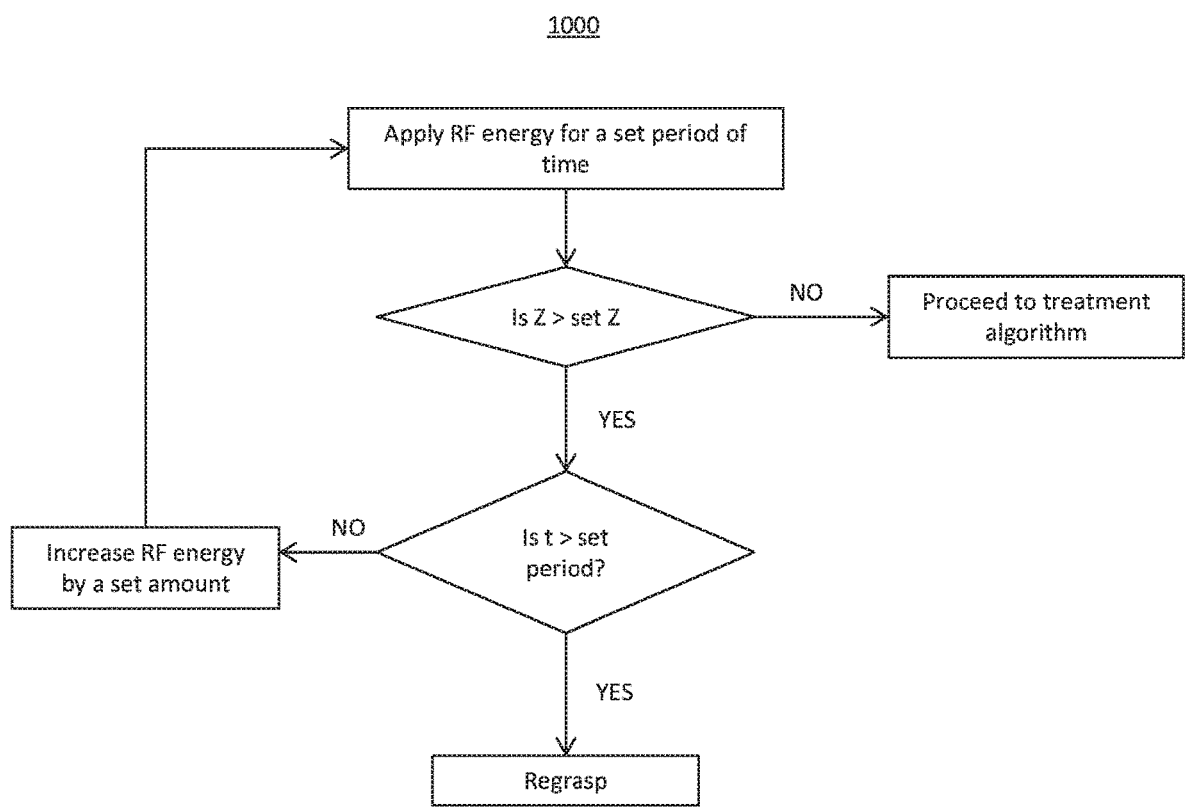
FIG. 10 is a flow chart of a method for applying a radio frequency waveform to achieve conductor breakthrough through a dielectric coating according to a further aspect of the present disclosure.

With reference to FIG. 10, a further embodiment of a pre-treatment algorithm for achieving conductor breakthrough in the non-stick coating 400 is shown as a flow chart 1000. Initially, the controller 724 signals the power converter 728 to output an RF waveform for a set period of time, which may be similar to the waveform of the algorithms of the flow charts 800 and 900. The RF waveform is applied for a period of time, which may be from about 50 msec to about 1 sec, and in embodiments, may be from about 100 msec to about 200 msec. The controller 724 continuously receives measured impedance from sensors of the generator 700 and compares the measured impedance to a set impedance that is indicative of achieving conductor breakthrough of the non-stick coating 400. The set impedance may be settable by the user or automatically by the generator 700 based on the type of forceps 10 connected to the generator 700. Similarly to the algorithms of the flow charts 800 and 900, the measured parameter and threshold may be voltage and/or current.

If the measured impedance drops below the set impedance, then the controller 724 proceeds to execute a treatment algorithm such as sealing algorithms disclosed in U.S. Pat. No. 8,147,485 and U.S. Patent Application Publication No. 2016/0045248 as incorporated by reference above. If the impedance is above the set threshold, then the generator 700 continues to apply the RF waveform until set time period expires.

The controller 724 maintains a timer for the application of the RF waveform and compares the measured time of the timer to the set time period. If the timer has not yet expired, namely, if the measured time is below the set time period, and the impedance does not drop below the set threshold (or if current and/or voltage does not exceed the set threshold), the generator 700 continues to apply the RF waveform until the set time period expires.

In addition, the controller 724 also increases a power setting of the RF waveform. In embodiments, the power intensity may be increased incrementally and periodically. More specifically, the power intensity of the RF waveform may be increased in any suitable increment, such as by about 5% of the initial power setting or discrete power amounts, such as from about 10 watts to about 40 watts, or in embodiments from about 20 watts to about 30 watts. The power setting increments may occur periodically, with each period being from about 5 msec to about 50 msec, in embodiments from about 10 msec to about 30 msec.

If the set time period expires, without the measured impedance dropping below the set threshold or without the measured current and/or voltage exceeding the set threshold, then the pre-treatment algorithm instructs the generator 700 to issue a retry alert, such as instructing the user to regrasp the tissue with the jaw members 110 and 120.

It will be appreciated that of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims. Unless specifically recited in a claim, steps or components of claims should not be implied or imported from the specification or any other claims as to any particular order, number, position, size, shape, angle, or material.

What is claimed is:

1. An electrosurgical system comprising:
an electrosurgical instrument including an electrode having a polymeric dielectric coating; and
an electrosurgical generator including:
a power converter configured to generate RF energy;
a sensor coupled to the power converter and configured to sense at least one parameter of the RF energy; and
a controller coupled to the sensor and the power converter, the controller configured to:
control the power converter to output an RF waveform to achieve conductor breakthrough through the polymeric dielectric coating;
determine whether the conductor breakthrough occurred based on the at least one parameter; and
execute a treatment algorithm based on a determination of the conductor breakthrough.

2. The electrosurgical system according to claim 1, wherein the controller is further configured to compare the at least one parameter to a set threshold indicative of the conductor breakthrough.

3. The electrosurgical system according to claim 2, wherein the controller is further configured to control the power converter to output the RF waveform for a set period of time.

4. The electrosurgical system according to claim 3, wherein the controller is further configured to execute the treatment algorithm based on the determination of the conductor breakthrough occurring within the set period of time.

5. The electrosurgical system according to claim 1, wherein the at least one parameter is measured impedance and the controller is further configured to compare the measured impedance to a set impedance threshold.

6. The electrosurgical system according to claim 5, wherein the controller is further configured to execute the treatment algorithm in response to the measured impedance being below the set impedance threshold.

7. The electrosurgical system according to claim 6, wherein the controller is further configured to adjust a power setting of the treatment algorithm prior to the execution of the treatment algorithm in response to the measured impedance being above the set impedance threshold.

8. The electrosurgical system according to claim 6, wherein the controller is further configured to adjust a power setting of the RF waveform in response to the measured impedance being above the set impedance threshold.

9. The electrosurgical system according to claim 1, wherein the at least one parameter is measured voltage and the controller is further configured to compare the measured voltage to a set voltage threshold.

10. The electrosurgical system according to claim 1, wherein the at least one parameter is measured current and the controller is further configured to compare the measured current to a set current threshold.

11. A method comprising:
electrically coupling an electrosurgical instrument to an electrosurgical generator, the electrosurgical instrument including an electrode having a polymeric dielectric coating;
controlling a power converter of the electrosurgical generator to output an RF waveform to achieve conductor breakthrough through the polymeric dielectric coating;
sensing at least one parameter of the RF waveform at a sensor of the electrosurgical generator;
determining at a controller of the electrosurgical generator whether the conductor breakthrough occurred based on the at least one parameter; and executing a treatment algorithm at the controller based on a determination of the conductor breakthrough.

12. The method according to claim 11, wherein determining whether the conductor breakthrough occurred further includes comparing the at least one parameter to a set threshold indicative of the conductor breakthrough.

13. The method according to claim 12, further comprising outputting the RF waveform for a set period of time.

14. The method according to claim 13, wherein the treatment algorithm is executed based on the determination of the conductor breakthrough occurring within the set period of time.

15. The method according to claim 11, further comprising:
    measuring impedance; and
    comparing the measured impedance to a set impedance threshold.

16. The method according to claim 15, further comprising executing the treatment algorithm in response to the measured impedance being below the set impedance threshold.

17. The method according to claim 16, further comprising adjusting a power setting of the treatment algorithm prior to the execution of the treatment algorithm in response to the measured impedance being above the set impedance threshold.

18. The method according to claim 16, further comprising adjusting a power setting of the RF waveform in response to the measured impedance being above the set impedance threshold.

19. The method according to claim 11, further comprising:
    measuring voltage; and
    comparing the measured voltage to a set voltage threshold.

20. The method according to claim 11, further comprising:
    measuring current; and
    comparing the measured current to a set current threshold.

* * * * *